United States Patent
Paz et al.

(10) Patent No.: US 6,640,649 B1
(45) Date of Patent: Nov. 4, 2003

(54) DROPLET COUNTER FOR LOW FLOW RATES

(75) Inventors: Ilan Paz, Gush Etzion (IL); Harold Jacob, Cederhurst, NY (US)

(73) Assignee: S.F.M. Sophisticated Flow Meters Ltd., Gush Etzion (IL)

( * ) Notice: Subject to any disclaimer, the term of this patent is extended or adjusted under 35 U.S.C. 154(b) by 0 days.

(21) Appl. No.: 09/889,206

(22) PCT Filed: Jan. 14, 2000

(86) PCT No.: PCT/IL00/00027

§ 371 (c)(1),
(2), (4) Date: Sep. 4, 2001

(87) PCT Pub. No.: WO00/42394

PCT Pub. Date: Jul. 20, 2000

(30) Foreign Application Priority Data

Jan. 14, 1999 (IL) ................................................. 128056

(51) Int. Cl.⁷ .............................................. G01F 13/00
(52) U.S. Cl. ................................................. 73/861.41
(58) Field of Search ....................... 73/861.41; 604/253, 604/245, 65, 67, 81; 324/439; 137/486; 340/609

(56) References Cited

U.S. PATENT DOCUMENTS

| | | | | |
|---|---|---|---|---|
| 3,641,543 A | * | 2/1972 | Rigby ................. 128/DIG. 13 |
| 3,712,132 A | * | 1/1973 | Low et al. .................. 324/439 |
| 3,859,854 A | | 1/1975 | Dye et al. ...................... 73/215 |
| 3,870,065 A | * | 3/1975 | Minns, Jr. ...................... 137/93 |
| 3,871,229 A | | 3/1975 | Fletcher ........................ 73/204 |
| 4,051,431 A | | 9/1977 | Wurster .................... 324/61 R |
| 4,099,412 A | | 7/1978 | Nehrbass ..................... 73/209 |
| 4,261,388 A | * | 4/1981 | Shelton ........................ 137/486 |
| 4,343,316 A | | 8/1982 | Jespersen ..................... 128/771 |
| 4,448,207 A | | 5/1984 | Parrish ........................ 128/771 |
| 4,484,582 A | | 11/1984 | Rottenberg et al. .......... 128/630 |
| 4,520,667 A | | 6/1985 | Nelson ........................ 73/171 |
| 4,532,936 A | | 8/1985 | LeVeen et al. ............... 128/762 |
| 4,554,687 A | | 11/1985 | Carter et al. .................. 4/144.2 |
| 4,559,831 A | | 12/1985 | Prestele .................... 73/861.05 |
| 4,650,464 A | * | 3/1987 | Ruiz et al. ................... 604/500 |
| 4,683,748 A | | 8/1987 | Carter ........................... 73/226 |
| 4,718,896 A | * | 1/1988 | Arndt et al. ................. 604/253 |
| 4,740,200 A | * | 4/1988 | Theeuwes .................... 604/85 |
| 4,827,766 A | | 5/1989 | Nelson ........................ 73/171 |
| 4,946,439 A | * | 8/1990 | Eggers ................ 128/DIG. 13 |
| 5,098,408 A | * | 3/1992 | Tarzian ........................ 251/125 |
| 5,571,964 A | | 11/1996 | Sawada et al. ............... 73/202 |
| 5,581,026 A | | 12/1996 | Sawada et al. ............... 73/202 |
| 5,698,793 A | | 12/1997 | Carmichael ............. 73/861.58 |
| 5,769,087 A | | 6/1998 | Westphal et al. ........... 128/760 |
| 6,447,684 B2 | * | 9/2002 | Parekh et al. ............... 210/638 |

* cited by examiner

*Primary Examiner*—Edward Lefkowitz
*Assistant Examiner*—Jewel V. Thompson
(74) *Attorney, Agent, or Firm*—Ladas & Parry

(57) ABSTRACT

A low-flow metering device 10 for measuring the flow of an amount of liquid exceeding 0.05 ml., in which a first chamber 12 has an inlet 14, and an outlet 16 in fluid communication with a second chamber 17, the first chamber 12 containing an element 22 creating a laminar flow 24. The outlet 16 of the first chamber is provided with a drop generator 19 leading to the second chamber 17 and is sized to release a series of droplets 18, each of the droplets forming and breaking away under its own weight from liquid in the drop generator orifice. An overflow conduit 21 extends between an upper area of the first chamber 12 and a lower area of the second chamber 17 for equalizing gas pressure between the two chambers 12, 17. An electronic system 28 is positioned in the second chamber 17 below the drop generator 19 for counting the passage of each droplet 18 exiting therefrom, and an information processing unit 32 is connected to the electronic system 28 for receiving and recording information.

19 Claims, 6 Drawing Sheets

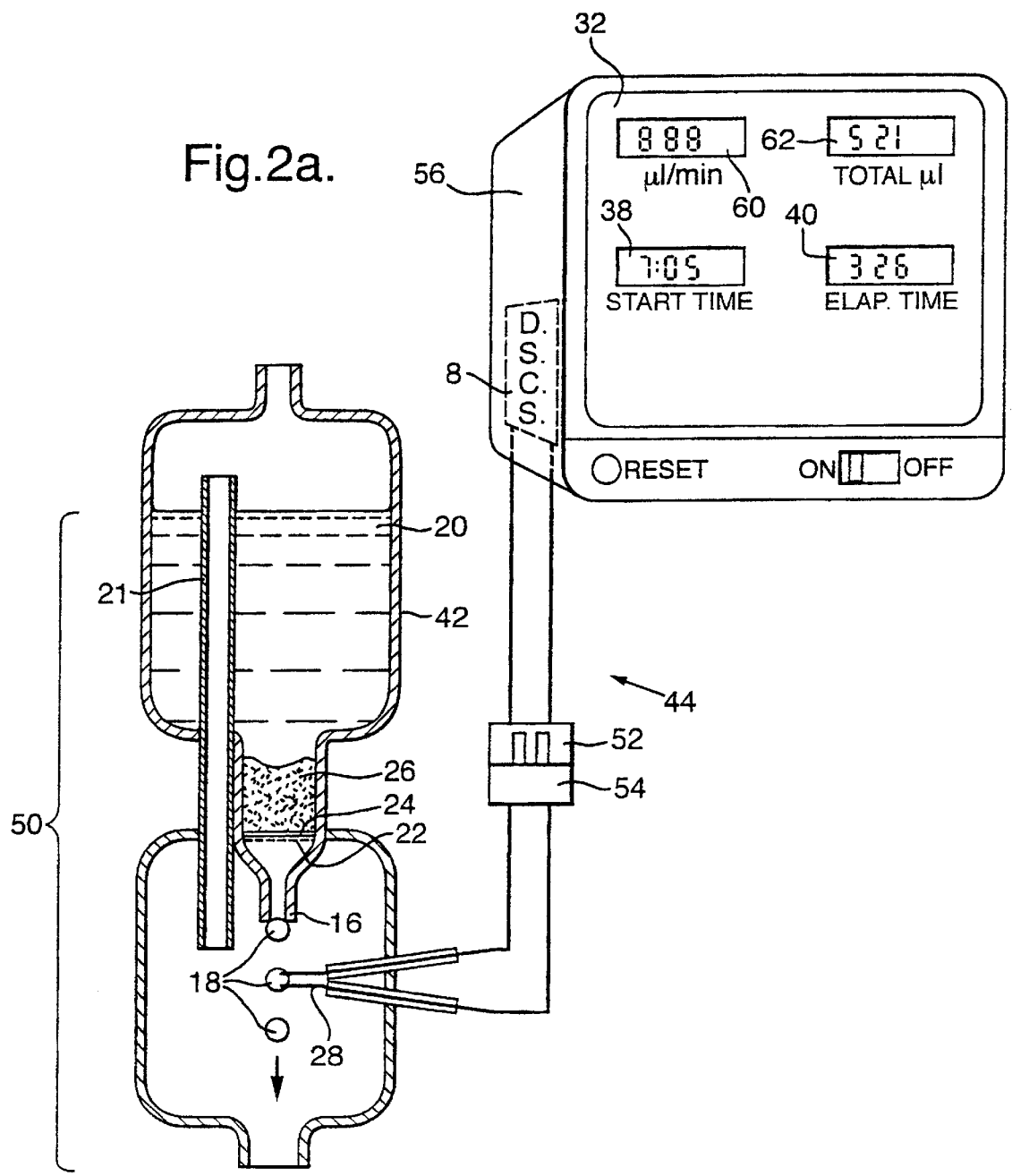

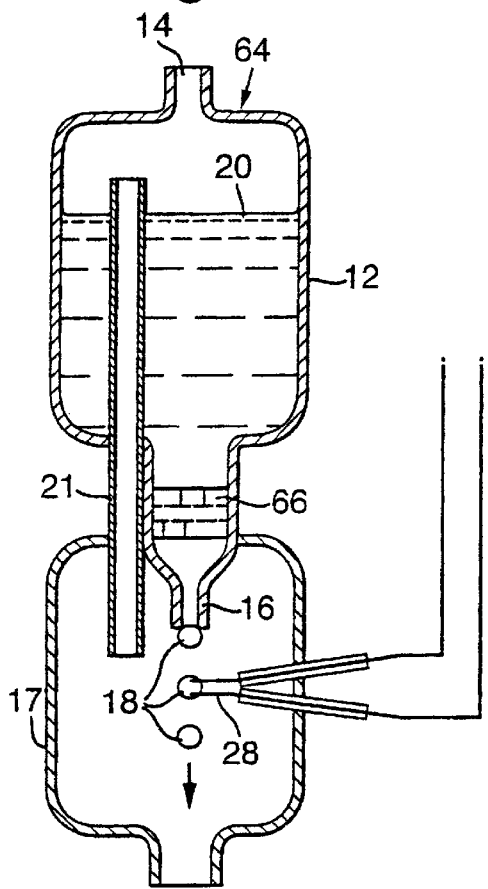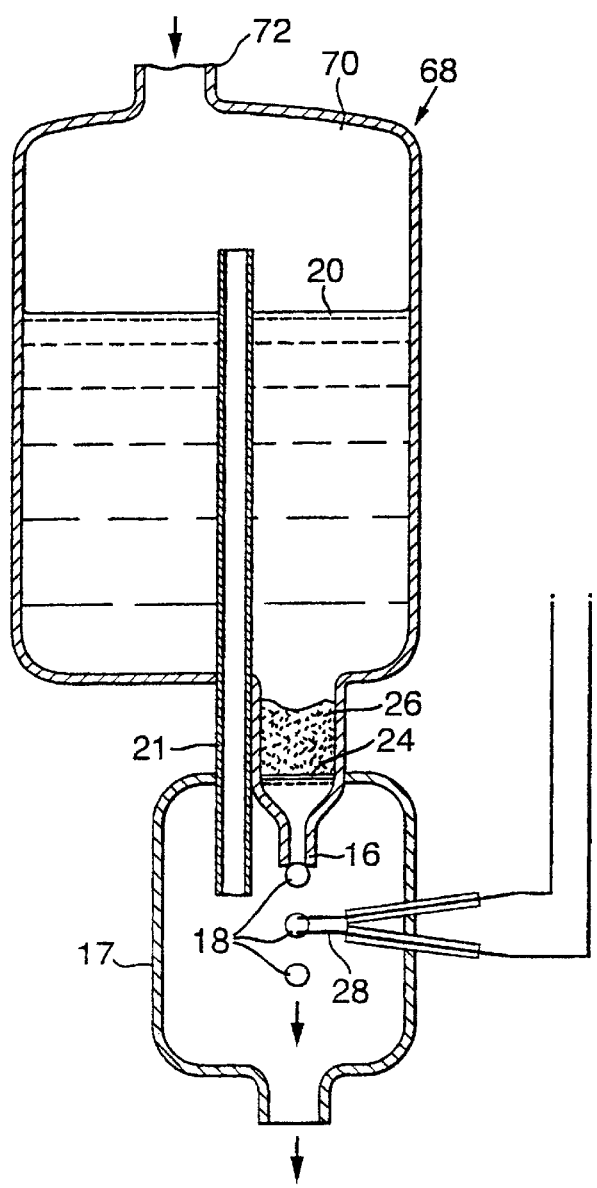

DROPLET COUNTER FOR LOW FLOW RATES

TECHNICAL FIELD

The present invention relates to liquid metering. More particularly, the invention provides a device capable of registering very low flows, being particularly useful in the laboratory and in medical applications, including intravenous infusions, blood flow control and urine output measurement.

BACKGROUND ART

Flow meters for liquids have many important applications such as furnishing information in medical applications, research, industrial and agricultural work. Known types of flow meter include the nutating-disk, lobed impeller, office flow obstruction, tapered tube rotameter, turbine, and magnetic types. The state of the art in flow meter development is represented by recent US Patents, among them U.S. Pat. Nos. 5,571,964 and 5,581,026 to Sawada et al., and U.S. Pat. No. 5,698,793 to Carmichael. Conventional types of flow meter become unreliable for low flows, and for very low flows which may be discontinuous no meaningful results are obtained. Yet there is a need for such measurements in applications such as for example for metering the urine output of some critical hospital patients.

In many hospitals it is common that the average urine flow is determined hourly by having a nurse or attendant examine the transparent graduated collection bag located below the bed of the patient. In intensive care departments such personnel are likely to be distracted by more urgent tasks and omit to take such measurements. The method is costly, unreliable and due to the flexible collection bag, also inaccurate.

Many special devices have been proposed. Among patent disclosures are devices for rainfall measurement and meters which are either intended for urine flow measurement or can be adapted for such purpose.

Dye et al. in U.S. Pat. No. 3,859,854 disclose an apparatus for measuring a liquid discharge, which includes a receptacle including a wall, a cup shaped pan, and a chamber below the pan. Liquid is accumulated in a compartment, and the height of the liquid is measured.

Wurster proposes a capacitance type of measurement for urine flow in U.S. Pat. No. 4,051,431. Using the urine as an electrical conductor and as a dielectric, the capacitance is used to derive the volume of urine present.

Nehrbass in U.S. Pat. No. 4,099,412 proposes to use a rotameter to measure the instantaneous flow rate of urine discharge.

In U.S. Pat. No. 4,484,582 Rottenberg et al. disclose a system for measuring flow of electrolytic fluids, wherein a pair of electrodes are flush with the surface of a cylindrical flow cell. A monopolar pulse train is applied across the electrodes to effect a cell impedance inversely proportional to the flow rate.

Jespersen describes optical sensor means to operate a lower and an upper valve described in U.S. Pat. No. 4,343,316. Intermittent discharge of a measured volume is used to indicate urine flow rate.

Parrish discloses an ultrasonic transceiver in a measuring system he describes in U.S. Pat. No. 4,448,207. The transceiver is arranged to periodically measure the height level of a urine column.

LeVeen discloses a meter based on an optical sensor in U.S. Pat. No. 4,532,936. A peristaltic pump is used to empty the measurement column at a known rate.

Carter et al. describes a pressure sensor in a funnel-shaped device described in U.S. Pat. No. 4,554,687. A pressure transducer produces an electrical signal in response to air pressure resulting from urine accumulation. He further details a second variation using a sealed vertical air column in U.S. Pat. No. 4,683,748.

A device intended for flow measurement of small liquid volumes is disclosed by Prestele in U.S. Pat. No. 4,559,831. He channels the liquid through a small diameter tube into which gas bubbles are also fed. By measuring the advance of the bubble, fluid flow rate can be deduced.

Westphal et al. suggest a force transducer to weigh collected urine in an apparatus described in U.S. Pat. No. 5,769,087.

Nelson proposes devices to measure rainfall by electronic drop counting in U.S. Pat. No. 4,520,667 and 4,827,766. The latter patent discloses a vent tube which is partially liquid immersed.

Most flow measuring systems measure some related parameter to deduce flow rate. However errors are introduced when the relationship between the measured parameter and the flow rate is not constant. Such relationship is often effected by temperature changes, and by changes in the fluid density and viscosity. Few prior-art systems are capable of measuring extremely low flows, such as a flow of a few drops per hour.

SUMMARY OF THE INVENTION

It is therefore one of the objects of the present invention to obviate the disadvantages of prior art flow meters and to provide an apparatus which is able to record flow of a few drops per hour.

It is a further object of the present invention to provide a flowmeter which meets the requirements for registering urine output of catheterized patients, and also for metering infusion rates.

DISCLOSURE OF THE INVENTION

The present invention achieves the above objects by providing a low-flow metering device for measuring the volume of an amount of liquid exceeding 0.05 ml., comprising:

a) a first chamber having an inlet, and an outlet in fluid communication with a second chamber, said first chamber containing a flow restriction element creating a laminar flow and said outlet of said first chamber being provided with a drop generator leading to said second chamber and sized to release a series of droplets, each of said droplets forming and breaking away under its own weight from liquid in the drop generator orifice fed thereto by said flow restriction element, b) an overflow conduit extending between an upper area of said first chamber and a lower area of said second chamber for equalizing gas pressure between said two chambers;

c) electronic means positioned in said second chamber below said drop generator for counting the passage of each droplet exiting therefrom; and d) an information processing unit connected to said electronic means for receiving and recording information and for measuring the time interval between successive droplets and for calculating flow rates and total volume therefrom while dealing with variations in droplet size as a function of the time interval between successive droplets.

In U.S. Pat. No. 3,641,543 (D1), there is described a low-level detector and drop rate monitor, particularly for intravenous feeding apparatus. This patent primarily relates to the electronic means of detecting the drops and fluid to be monitored and relates only briefly to the mechanical apparatus which is of little importance to the invention described in said patent. While the drawing in FIG. 1 in said patent, shows the provision of an air line 11, in fact said patent does not teach or suggest the device of the present invention to a person skilled in the art since the device as shown in said figure, does not work. Specifically, since air line 11 extends into an inverted bottle which has no inlet, as the liquid flows therefrom a vacuum is created in the upper portion of container 12 which will balance against the force of gravity and not permit complete flow of the liquid from said bottle. Furthermore, valve mechanism 20 is separate from the drop formation opening and if said valve is closed the drops will fall until they fill the second chamber whereby electrodes 38 and 40 will be unable to measure any drop formation. Finally, said patent does not teach or suggest the arrangement of the present invention, wherein the flow restriction element leads directly to the drop generator and instead in said patent, and in other patents discussed hereinafter, the flow restriction element 20 is in fact positioned in the line after the drop generator. Therefore, said patent neither teaches nor suggests the present device.

U.S. Pat. No. 5,098,408 (D2), teaches the use of an automatic intravenous flow controller wherein the primary purpose is to restrict the flow in a controlled way. In said patent, drops are formed along the outer surface of an icicle or stylus drop former positioned in fluid communication between an inlet and outlet end of the flow controller. These drops break away from the material of the icicle and the surface tension between the icicle and the fluid determines the size of the drops. The drops are not counted and the drops only serve as a rough visual indication of flow rate. In contradistinction, according to the present invention, the drops are formed within the drop generator and each droplet breaks away under its own weight from liquid in the drop generator orifice, i.e. by the breaking of liquid-liquid surface tension.

U.S. Pat. No. 4,520,667 (D3), teaches a non-mechanical digital rain gauge. As can be seen from the description in column 5 of said patent, the device is designed in such a manner that there will never be more than 2 rain drops entering the opening thereof in a second. Therefore, no flow restriction device is required or taught and each drop that enters the device passes into the drop generator and is counted.

U.S. Pat. No. 3,871,229 (D4), teaches a drop sensing apparatus with a flow restriction device positioned along the tube feeding the needle. While flow may be corrected by said flow restriction device, as a result of the drop rate, this patent neither teaches nor suggests an arrangement wherein the flow restriction element leads directly to the drop generator.

In U.S. Pat. No. 3,712,132 (D5), there is described a droplet monitoring probe which comprises 2 electric wires spaced a known distance apart from each other and connected at one end to means for establishing a DC potential between the wires. A drop in the fluid stream momentarily contacts both wires causing an electrical signal, which may be counted. These droplets, however, are not falling droplets and instead, are droplets forming and flowing in a gas turbine.

In U.S. Pat. No. 4,261,388 (D6), there is described a drop rate controller for controlling flow of fluid from an infusion fluid reservoir to an intravenous infusion site apparatus with a flow restriction device positioned along the tube feeding the infusion site. While flow may be corrected by said flow restriction device, as a result of the drop rate, this patent neither teaches nor suggests an arrangement wherein the flow restriction element leads directly to the drop generator.

Thus it will be realized that none of said patents teaches or suggests a low-flow metering device as described and claimed herein, wherein the flow restriction element leads directly to the drop generator and wherein there is provided means for measuring the time interval between successive droplets and for calculating flow rates and total volume therefrom while dealing with variations in droplet size as a function of the time interval between successive droplets.

It will be understood that the novel device of the present invention. serves to measure flow even when fluid supply is non-continuous. As even a single droplet is registered by the electrodes or optical means, and there is no practical limit to the time span between one droplet and the next, very low flow rates can be reliably metered. Applications include infusions, urine output, rainfall measurement, patient's blood input or output, patient feeding with liquids, and determining the results of overhead irrigation in agriculture.

The invention provides means for measuring the time interval between successive droplets, and calculates flow rates therefrom. It is realized that the size of the droplets may change in relation to said time interval. Means for dealing with variation in droplet size are provided as will be seen with reference to FIGS. 2a and 2b.

Furthermore, an embodiment of the invention, described with reference to FIG. 7 is able to recognize very fast inflow causing overflow and to report such condition, as well as being able to report a full collection bag, and to activate an alarm if needed.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE FIGURES OF THE DRAWING

FIG. 2a is a diagrammatic view of an embodiment part of which is disposable;

FIG. 3 is a diagrammatic view of part of an embodiment including a flow regulator and a labyrinth drop generator;

FIG. 4 is a diagrammatic view of part of an embodiment including a feed reservoir.

DETAILED DESCRIPTION OF THE INVENTION

Figure 1:
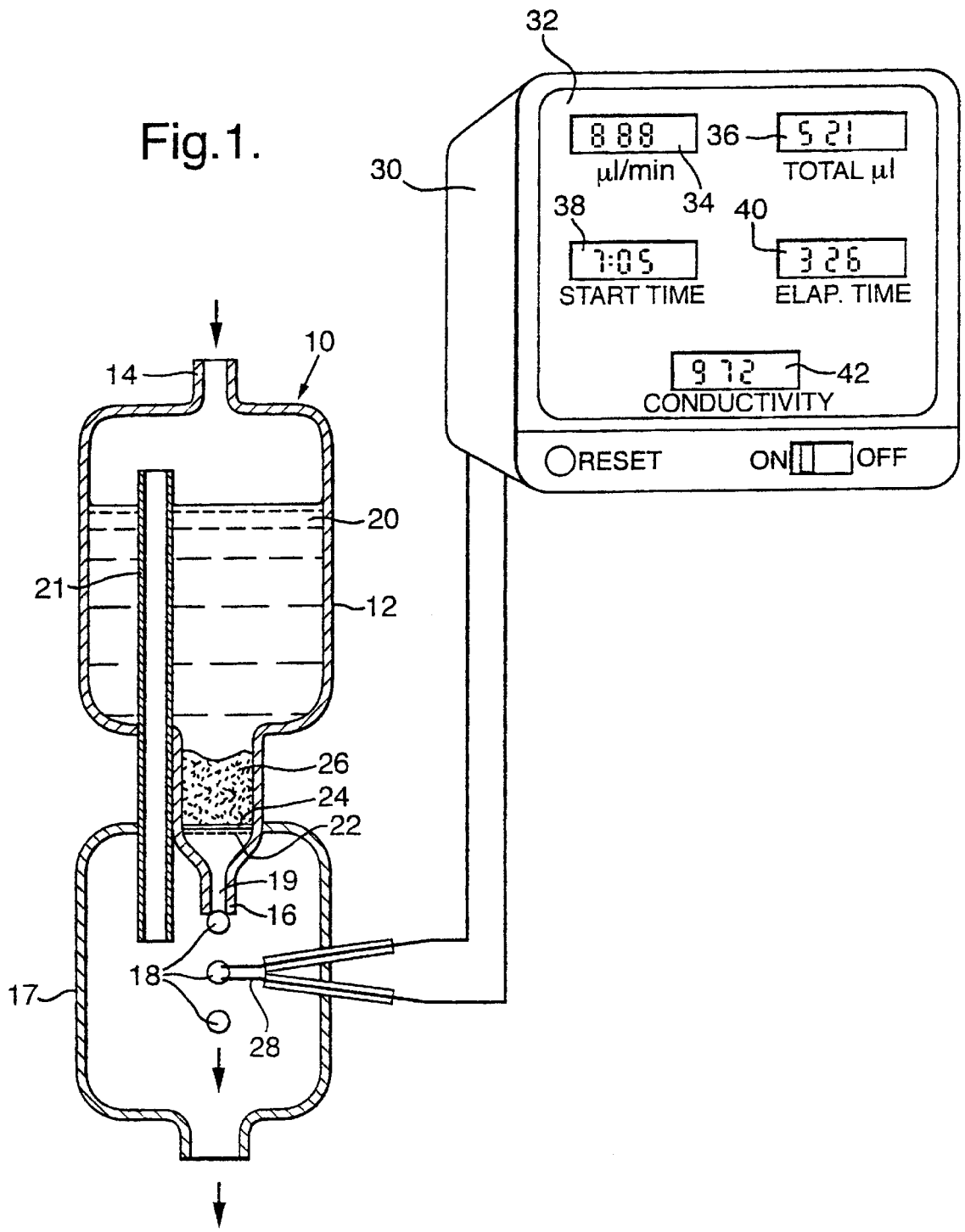
FIG. 1 is a diagrammatic view of a preferred embodiment of the metering device according to the invention.

There is seen in FIG. 1 a low-flow metering device 10. The flow range which can be detected is typically from about 0.05 ml, that is about one droplet, up to about 6 liters, per hour.

A first chamber 12 has an inlet 14, and an outlet 16 in fluid communication with a second chamber 17. The first chamber 12 has an upper reservoir chamber 12A and a lower drop generator chamber 12B from which orifice 16 extends. Preferably the diameter of the orifice 19 of outlet 16 is smaller than the diameter of the inlet 14. Advantageously the diameter of the outlet orifice 19 is between about 3 and 6 mm, as such a size is suitable for forming droplets 18 when a liquid 20 having a viscosity similar to water is passed therethrough. However, the outlet 16 is larger for handling more viscous fluids such as oil.

The first chamber 12 contains an element creating a laminar flow, which in the present embodiment comprises a porous substance 24 supported by a screening element 22. Suitably, the porous substance 24 is a fibrous mat. Granular particles 26, for example sand, may be used either alone or in combinations with the mat 24 as shown.

The outlet 16 of the first chamber 12 acts as a drop generator leading to the lower second chamber 17. The outlet 16 is sized to release a series of droplets 18, each droplet 18 forming and breaking away under its own weight from liquid in the drop generator chamber 12B and orifice 19.

An overflow conduit 21 extends between an upper area of the first chamber 12 and a lower area of the second chamber 17. One of the functions of the conduit 21 is to equalize gas pressure between the two chambers 12, 17.

The conduit 21 also prevents flooding of the upper area in case of unexpectedly fast inlet flows.

Electrodes 28 are positioned in the second chamber 17 in spaced-apart relationship one above the other below the outlet orifice 16. This arrangement allows operation of the device 10 even if installed slightly off the vertical axis. Electrodes 28 count and time the passage of each droplet 18 passing and contacting electrodes 28. In the present embodiment a voltage is applied between the electrodes 28, and the resulting current is recorded. Current is practically zero when no droplet is present between electrodes 28, but does flow when a droplet 18 is in contact and bridges the electrodes 28.

If fluid conductivity is of interest the current value is recorded. If this is not required, the current is merely recorded as a pulse, which is counted electronically. Droplet counting is done by an information processing unit 30 electronically connected to the electrodes 28 for receiving and recording information.

The information shown on the display 32 includes flow per unit time 34. Additionally the display shows total flow 36, start time 38, and elapsed time 40.

In the present embodiment electrical conductivity of the fluid passing between the electrodes is also shown 42. Electrical conductivity is an indicator of substances present in liquid 20 which, for example with urine, may be of interest to medical staff.

With reference to the rest of the figures, similar reference numerals have been used to identify similar parts.

Referring now to FIG. 2a, there is seen a low-flow metering device 44 particularly useful for medical purposes.

The upper chamber 42, the lower chamber 46 and the electrodes 48 are part of a self-contained disposable unit 50. Electrical connection means, such as a socket 52 and plug 54, provide the connection so the information processing unit 56. Present hospital practice is to make increasingly wide use of disposable items, as the costs and risks associated with sterilization and reuse are high, and sterilization procedures are used mainly for high-cost metal items.

Figure 2B:
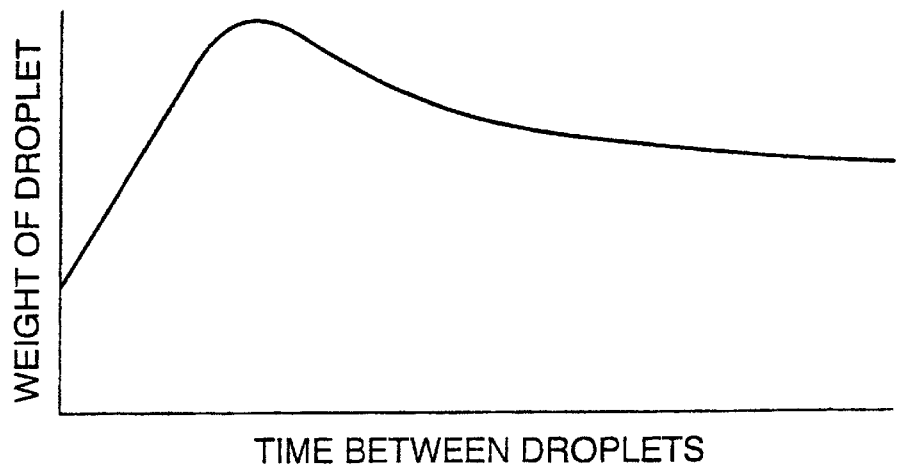
FIG. 2b is a representation of the relationship between drop size and time between drops.

In the present embodiment 44 measurement accuracy is enhanced by the addition of a drop size correction mechanism 58. Drop size varies as a non-linear function of time after separation of the previous drop. This relationship is illustrated in FIG. 2b, and this relationship is stored in an electronic look-up table included in the mechanism 58. The information processing unit 56 is in receipt of information as to the timing of drop release, and includes a correction mechanism based on this relationship which electronically adjusts the reported output flow 60 and volume 62 after correction.

FIG. 3 illustrates a part of a low-flow metering device 64 similar to that seen in FIG. 1.

In the present embodiment the element creating a laminar flow is a molded plastic labyrinth 66, which slows liquid flow while remaining resistant to blockage by solid particles below the size of the labyrinth passages.

Seen in FIG. 4 is a low-flow metering device 68 generally similar to that seen in FIG. 1.

A reservoir bag 70 is positioned between a source of liquid 72 and the drop generator 16,24,26. The bag 70 acts as a buffer between an intermittently fast input source 72 and the slow continuous discharge through output orifice 16. For urine monitoring, a bag up to 400 ml is usually suitable.

Figure 5:
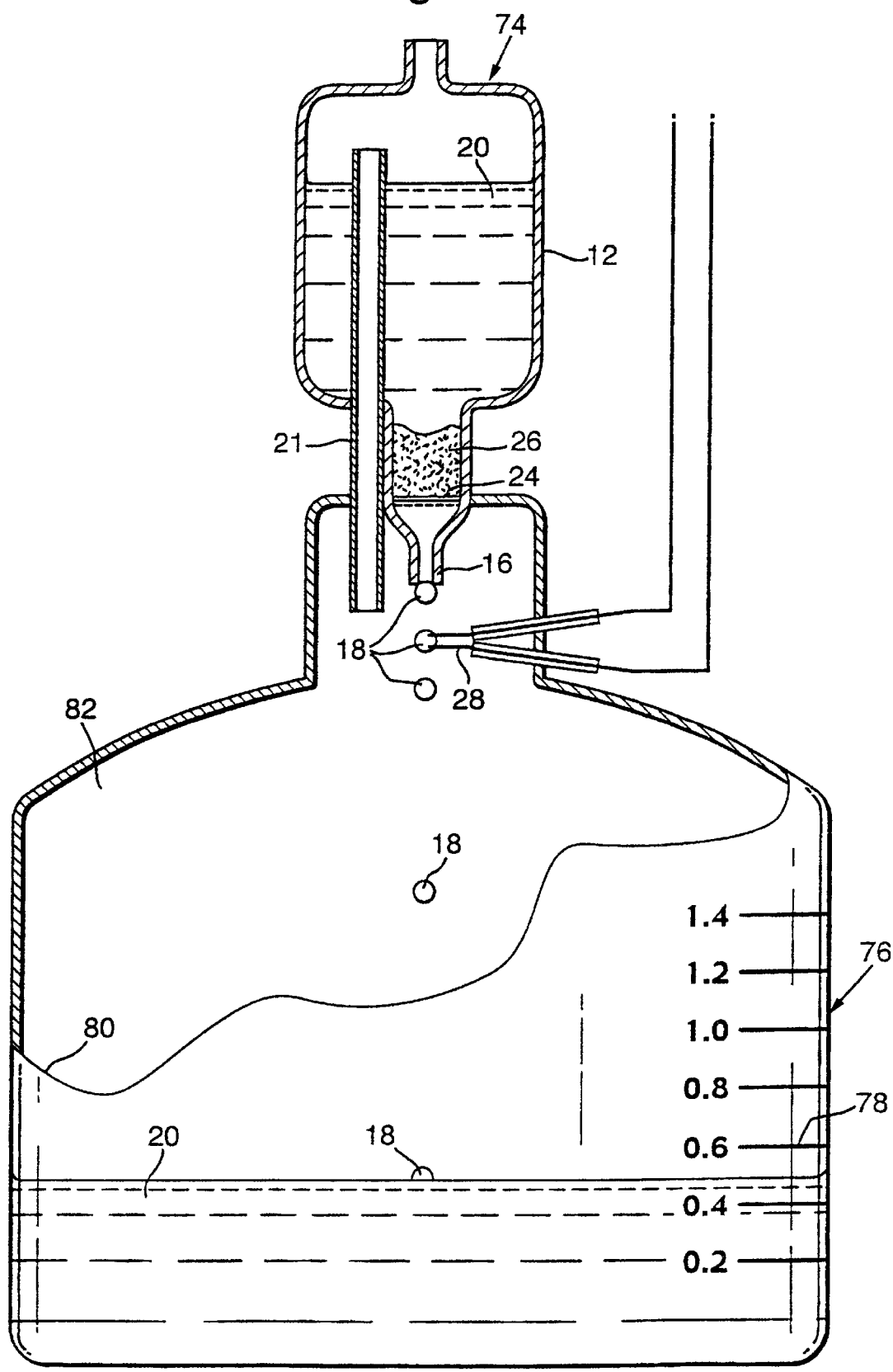
FIG. 5 is a diagrammatic view of part of an embodiment including a collection bag.

Referring now to FIG. 5, there is depicted a part of a low-flow metering device 74, further comprising a calibrated collection bag 76 positioned to receive droplets 18 after their passage between electrodes 28. The collection bag 76 has calibrations 78 and so provides a useful check on the information recorded electronically by the display 32 seen in FIG. 1. In the present embodiment the bag 76 has a 1.5 liter capacity, a transparent front 80, and a white opaque back 82 for convenience of observing liquid 20 collected therein.

Figure 6:
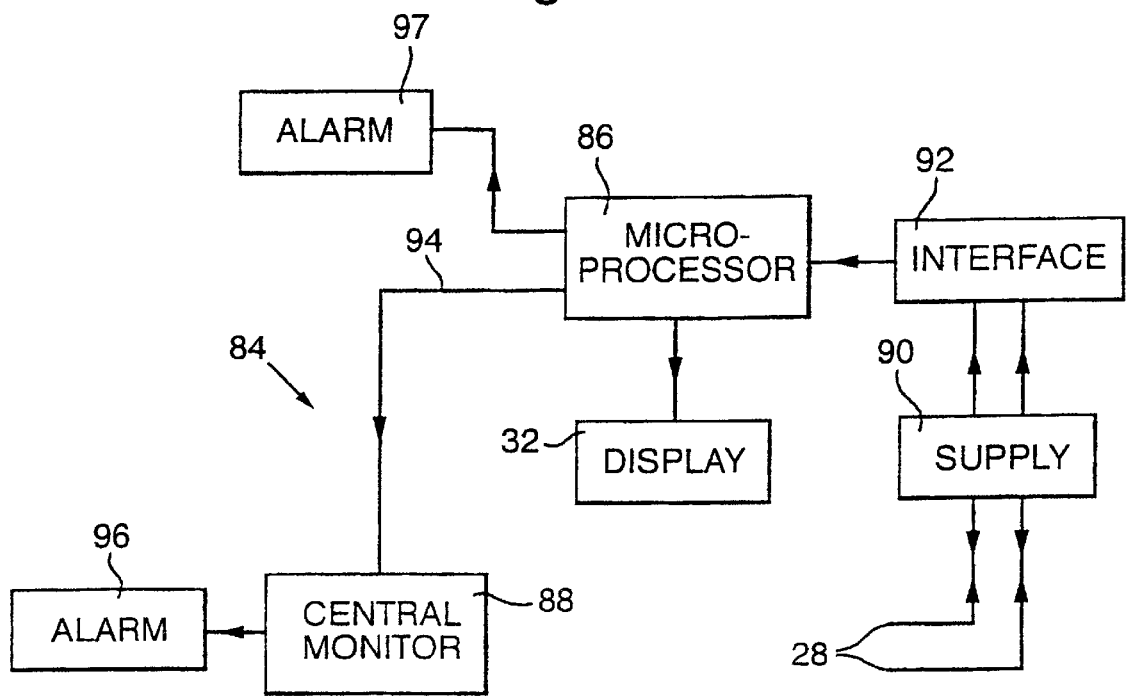
FIG. 6 is a block diagram of a system including a central monitor.

FIG. 6 shows a low-flow metering device 84 further comprising means for communicating information from the processing unit 86 to a central monitor 88. The processing unit 86 is a microprocessor which includes a clock and an arithmetic logic unit, and may also include the drop size correction mechanism 58 described with reference to FIGS. 2a and 2b. Electrodes 28 receive a voltage from a supply 90. Current measurements from an electrode 28 are made and converted to digital form in the interface 92. Information is sent by cable 94, as shown in the present embodiment, or by infra-red signals. The central monitor 88 is of particular value in intensive care units, where a nurse is charged with the supervision of multiple patients. The central monitor 88 is connected to an alarm 96 which is triggered by data readings which require immediate action by the nursing staff. Additionally an alarm 97 connected to microprocessor 86 is provided at the site where flow measurement is being carried out.

Figure 7:
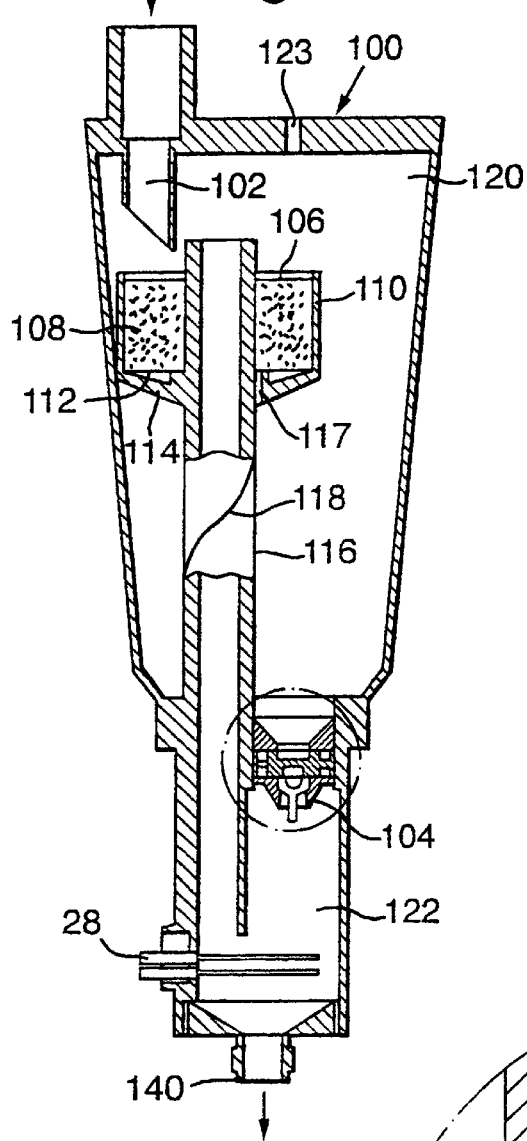
FIG. 7 is a sectional elevation of a further preferred embodiment.

FIG. 7 shows an embodiment of the low-flow metering device 100 having three flow paths.

A first path starts at the upper face of a filter element 108, which receives an ultra-low flow from the inlet 102. The filter element 108 has porous outer walls 110, the purpose of which will become apparent from the description of the second flow path. The third flow path refers to flows above design range. The first flow path leads to the filter element lower face 112, into a filter support cup 114. The flow path continues through a lower aperture 117 at the base of the cup 114. The droplets following this path next run down the outer face of a vertical tube 116, and from there enter the drop generator 104. The tube outer face is advantageously provided with a groove 118 to facilitate descent of the droplet.

The tube 116 serves three further purposes:
 a) it equalizes air pressure between the upper 120 and lower 122 parts of the chamber, which is helpful for obtaining consistent readings;
 b) it supports the filter cup 114; and
 c) it prevents flooding of the upper chamber 120 by serving as an overflow tube in case the device is subjected to fast flows for which it is not intended.

The second flow path leads from the upper face 106 to the filter element 108, through a part of said element, and out through the filter element porous wall 10. Discharge through the wall 110 occurs as the filter element 108 intentionally is made with a limited through-flow capacity. The second flow path continues into the upper chamber 120 and the into the drop generator 104

The third flow path refers to overload conditions. If input is so fast that the upper chamber 120 is almost full, the excess drains down inside tube 116. The excess fluid is however directed over the electrodes 28, which sense unusually long liquid contact and report overflow and/or sound an alarm.

Outlet 140 can be connected to a collection bag 76, seen in FIG. 5. Should the collection bag 76 be full and, due to an attendant not having replaced the full bag with an empty bag, a portion of the lower part of the chamber 122 will be flooded. Electrodes 28 register the presence of a continuous supply of fluid and activate an alarm 96 seen in FIG. 6. However as air is trapped between the fluid entering the housing outlet 140 and the drop generator 104, flooding of the drop generator 104 is prevented. Consequently, after the collection bag 76 is exchanged for an empty bag, flow measurements will proceed immediately without significant errors.

The upper part 120 of the chamber is provided with an air vent 123.

Figure 8:
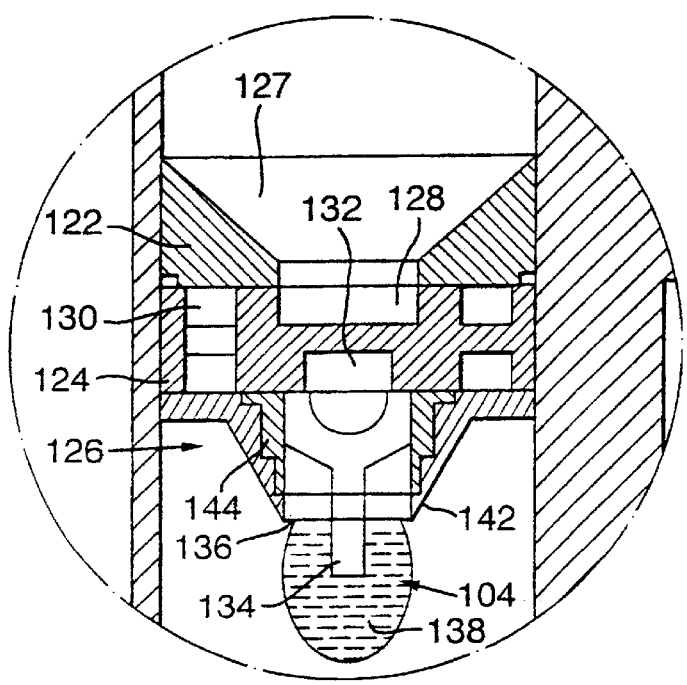
FIG. 8 is a detail of the drop generator seen in FIG. 7.

Seen in detail in FIG. 8 is the drop generator 104 which comprises three stacked components 122, 124, and 126.

An upper inlet funnel 127 receives fluid from either or both the flow paths described with reference to FIG. 7, and directs the liquid to the intermediate section 128 into the labyrinth inlet 124. The labyrinth 130 allows low flows to pass normally, but slows down flows which are too fast for direct conversion into discrete drops. The labyrinth outlet 132 is arranged to pass fluid to a lower section 126. A drop-direction pin-like element 134 extends downwardly from the center of the outlet orifice 136. A drop forming on the pin 134 falls when its size and weight are sufficient to overcome the surface tension of the fluid. The drop 138 falls to contact electrodes 28 and is then discharged through the chamber outlet 140.

Preferably the external wall 142 of the lower section 126 of the outlet orifice 136 is made of a hydrophobic material such as fluorinated ethylene propylene. This prevents the drop 138 from backing up the external wall 142.

However the inner lining 144 of the lower section 126 of outlet orifice 136 and the internal parts of the labyrinth are preferably made of a hydrophilic material, for example polyethersulfone. Thereby fluid flow is eased, entrained air bubbles are released, and the pin 134 receives fluid in an orderly manner.

While not shown, multiple drop generators, according to the present invention, can be arranged in parallel to monitor high flows.

While not shown in the figures, vent means can also be provided for one or more of the chambers, if desired.

It will be evident to those skilled in the art that the invention is not limited to the details of the foregoing illustrative embodiments and that the present invention may be embodied in other specific forms without departing from the scope of the claims. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A low-flow metering device for measuring the volume of an amount of liquid exceeding 0.05 ml., comprising:
 a) a first chamber having an inlet for introduction of liquid into said first chamber, and an outlet in fluid communication with a second chamber, said first chamber being divided into an upper reservoir chamber and a lower drop generator chamber and orifice, said reservoir chamber and lower drop generator chamber being interconnected by an intermediate flow restriction element creating a laminar flow, said outlet of said first chamber being provided with a drop generator leading to said second chamber and sized to release a series of droplets, each of said droplets forming and breaking away under its own weight from liquid in the drop generator chamber via said drop generator orifice,
 b) an overflow conduit extending between an upper area of said first chamber and a lower area of said second chamber for equalizing gas pressure between said two chambers;
 c) electronic means positioned in said second chamber below said drop generator for counting the passage of each droplet exiting therefrom; and
 d) an information processing unit connected to said electronic means for receiving and recording information and for measuring the time interval between successive droplets and for calculating flow rates and total volume therefrom while dealing with variations in droplet size as a function of the time interval between successive droplets.

2. A low-flow metering device according to claim 1, wherein the internal diameter of said drop generator orifice is between about 3 and 6 mm.

3. A low-flow metering device according to claim 1, wherein said electronic means comprise a pair of electrodes positioned in spaced-apart relationship one above the other below said orifice of said drop generator.

4. A low-flow metering device according to claim 3, wherein said first chamber, said second chamber, said drop generator and said electrodes are part of a self-contained disposable unit having electrical connection means for connection to said information processing unit.

5. A low-flow metering device according to claim 1, wherein said drop generator is provided with a drop-direction pin-like element extending downwardly from the center of the outlet orifice thereof.

6. A low-flow metering device according to claim 5, wherein said drop generator comprises an inlet funnel, an intermediate labyrinth section in which a labyrinth inlet can receive liquid from said funnel and a labyrinth outlet is arranged to direct said liquid into said drop generator chamber to said pin-like element extending downwardly from said outlet orifice.

7. A low-flow metering device according to claim 5, wherein outer surfaces of said outlet orifice are made of a hydrophobic material.

8. A low-flow metering device according to claim 7, wherein said material is fluorinated ethylene propylene.

9. A low-flow metering device according to claim 6, wherein internal parts of said labyrinth section and inner surfaces of said outlet orifice are lined with a hydrophilic material.

10. A low-flow metering device according to claim 9, wherein said material is polyethersulfone.

11. A low-flow metering device according to claim 1, wherein said element creating a laminar flow is a porous substance supported by a screening element.

12. A low-flow metering device according to claim 11, wherein said porous substance is selected from the group consisting of a fibrous mat, granular particles and combinations thereof.

13. A low-flow metering device according to claim 1, wherein said element creating a laminar flow is a molded plastic labyrinth.

14. A low-flow metering device according to claim 1, wherein a first path for liquid is provided from said first chamber inlet to said drop generator for ultra-low flows and a second path is provided for normal flows;

said first path starting at the upper face of a filter element provided with porous outer walls, leading to the filter element lower face, into a filter support cup, through an aperture at the bottom of said cup, down the outer face of said overflow conduit and into said drop generator; and said second path starting at said upper face of said filter element leading through said porous outer walls, through said first chamber and into said drop generator.

15. A low-flow metering device according to claim 1, further comprising a calibrated collection bag positioned to receive said droplets after passage from said inlet through said electronic means positioned in said second chamber.

16. A low-flow metering device according to claim 1, further comprising means for communicating information from said information processing unit to a central monitor.

17. A low-flow metering device according to claim 15, wherein said calibrated collection bag accumulates the liquid introduced through said inlet and has calibration indications thereon to indicate a quantity of liquid introduced into the device and accumulated in said bag.

18. A low-flow metering device according to claim 1, wherein said information processing unit measures total volume of liquid introduced in said inlet.

19. A low-flow metering device according to claim 18, wherein said device provides information related to urine flow of a patient.

* * * * *